United States Patent
Igreja

(10) Patent No.: US 6,250,136 B1
(45) Date of Patent: Jun. 26, 2001

(54) MOLTEN GLASS VISCOSITY AND/OR LEVEL METER

(76) Inventor: Virgilio dos Reis Cardoso Igreja, Avenida do Brasil, 17-8°, P-1700 Lisboa (PT)

( * ) Notice: Subject to any disclaimer, the term of this patent is extended or adjusted under 35 U.S.C. 154(b) by 0 days.

(21) Appl. No.: 09/254,017
(22) PCT Filed: Jun. 26, 1998
(86) PCT No.: PCT/PT98/00004
  § 371 Date: Feb. 26, 1999
  § 102(e) Date: Feb. 26, 1999
(87) PCT Pub. No.: WO99/01741
  PCT Pub. Date: Jan. 14, 1999

(30) Foreign Application Priority Data

Jul. 1, 1997 (PT) ............ 102023

(51) Int. Cl.⁷ ............................ G01N 11/16
(52) U.S. Cl. ............ 73/54.24; 73/54.28; 73/54.33
(58) Field of Search .................. 73/54.24, 54.28, 73/54.33, 54.26, 53.01

(56) References Cited

U.S. PATENT DOCUMENTS

| | | | |
|---|---|---|---|
| 2,668,442 | * 2/1954 | Osbourne | 73/59 |
| 3,062,040 | * 11/1962 | McKennell et al. | 73/59 |
| 3,131,515 | * 5/1964 | Mason | 51/58 |
| 3,162,038 | * 12/1964 | Roberson et al. | 73/59 |
| 3,712,117 | * 1/1973 | Fitzgerald et al. | 73/59 |
| 4,488,427 | * 12/1984 | Matusik et al. | 73/59 |
| 4,524,610 | * 6/1985 | Fitzgerald et al. | 73/54 |
| 4,905,499 | * 3/1990 | Miura et al. | 73/32 A |
| 5,067,344 | * 11/1991 | Fitzgerald et al. | 73/54 |
| 5,670,709 | * 9/1997 | Gallagher | 3/54.24 |
| 5,987,970 | * 11/1999 | Ball | 73/54.28 |

* cited by examiner

Primary Examiner—Hezron Williams
Assistant Examiner—David J. Wiggins
(74) Attorney, Agent, or Firm—Tilton, Fallon, Lungmus & Chestnut

(57) ABSTRACT

A device for the on-line measurement of viscosity and/or level of molten glass, converting the values of these variables into proportional electrical signals. The device comprises one sensor head connected to an electronic control unit and to a data processing unit. The sensor head comprises a fixed metallic core with external fins for air cooling, laid across by two vertical parallel shafts designed for torsional vibration to which are fixed, at the lower extremities, refractory rods partially coated with platinum and, at the upper extremities, the rotors of the two electrical motors which can produce torsional vibration of the vertical shafts. To each shaft are fixed two discs, connected mechanically to the fixed core by three fine rods disposed at 120° angles around the shaft. In operation, the sensor head is installed on a rigid structure fixed over the channel where the molten glass flows, with both rods partially immersed into the melt in order to be protected by the platinum coatings.

3 Claims, 1 Drawing Sheet

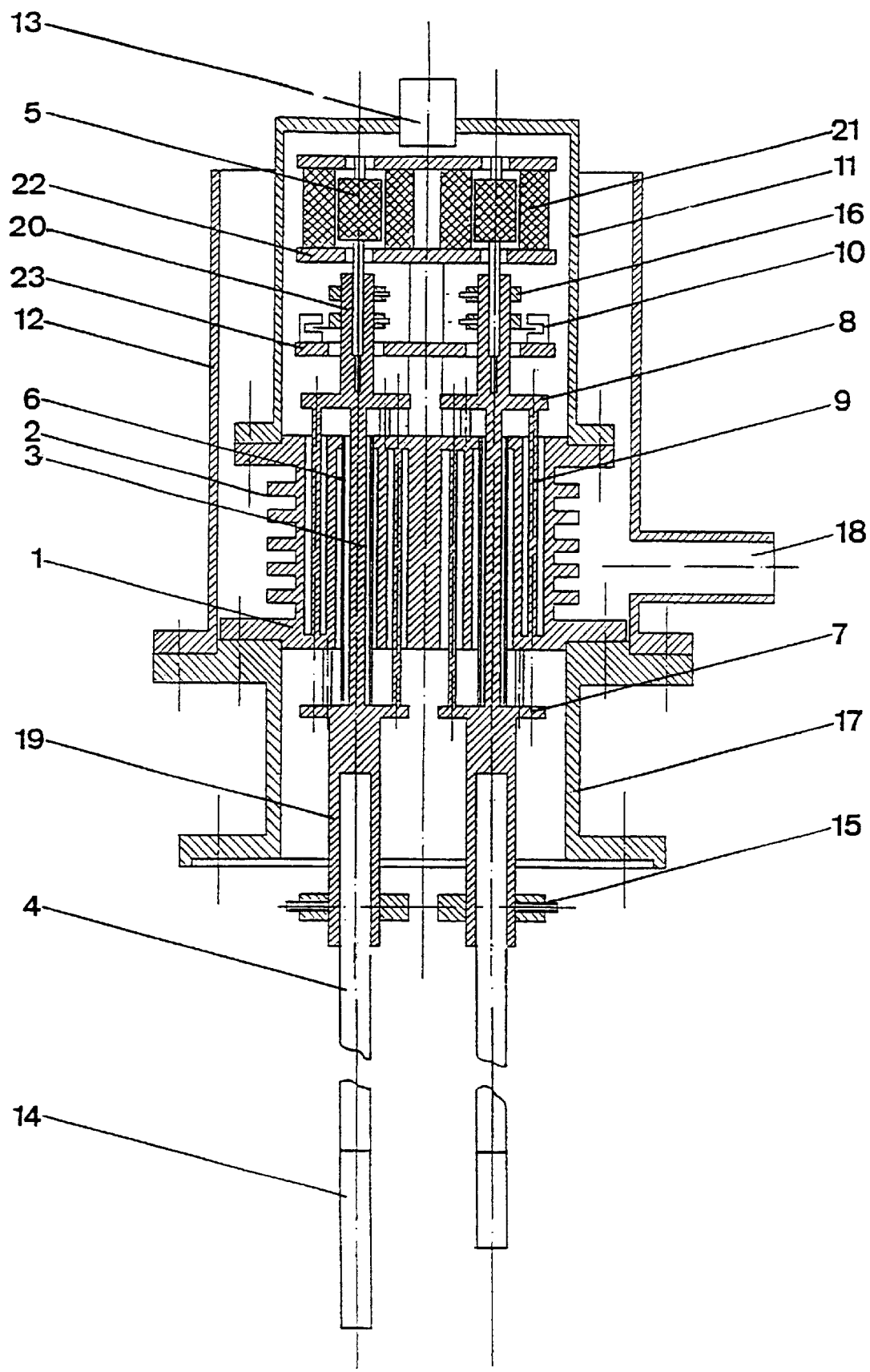

MOLTEN GLASS VISCOSITY AND/OR LEVEL METER

This invention relates to a new device for the on-line measurement of viscosity and/or level of molten glass. More particularly the invention relates to a new device for the simultaneous measurement of viscosity and level of molten glass, supplying correspondent electrical outputs proportional to the measured values. The invention is particularly advantageous as applied to the measurement of the viscosity and level of the melting in the feeders of forming machines, as referred below, but is also applicable to other branches of industry where the measurement of those variables is necessary.

As a matter of fact, one of the most critical processes in the glass manufacture is the preparation of the molten glass for delivery to the forming machines. The ultimate measure of the forehearth performance is constancy of weight per unit of delivered molten glass. This weight depends on glass level and glass viscosity. Temperature is currently employed as an indirect way of measuring viscosity. However glass viscosity is not only temperature—but also composition, type and quantity of cullet, water content in the raw materials, etc.—dependent. Therefore the direct viscosity measurement of the molten glass is of crucial importance.

It is a principal object of the invention, therefore, to provide a new on-line device for the direct measurement of viscosity of molten glass with an electrical output proportional to the measured value.

It is another object of the invention to provide associated means to the device which turns the measured value of viscosity independent of eventual variations of the level of the molten glass.

A further object of the invention is to provide associated means to the device in order that the level of the molten glass can be simultaneously measured and the correspondent values converted into electrical output signals.

SUMMARY OF THE INVENTION

The viscosity and/or level on-line meter for molten glass in accordance with the invention comprises one sensor head connected electrically to an electronic control unit and to a data processing unit. The sensor head comprises a fixed metallic core with external fins for air cooling, laid across by two vertical parallel shafts designed for maintaining a torsional vibration, to which are fixed, at the lower ends, refractory rods, and at upper ends, the rotors of two electrical motors designed to produce torsional vibration to the vertical shafts. The crossing of the core by each of the shafts is done by a torque tube in order that a mechanical sealing is formed between its lower end to which is fixed the refractory rod, and the upper end to which is fixed the rotor of each of the two motors. In order that each shaft could stand up against lateral efforts not tolerable by the simple associated torque tube, as those transmitted by the partially immersed rods in the molten glass, two metallic discs are fixed, just at the upper and lower ends of each shaft, each disc being mechanically connected to the fixed core through three fine rods disposed at 120° angles around the central shaft. On the upper end of each shaft it is fixed one conventional sensor of angular position in relation to the core. These sensors and the motors are closed into an air-tight case, fixed to the core, the whole being covered by a metallic sleeve prepared to receive pressurized cooling air. Through a multi-contact plug the inside elements are electrically connected to the exterior electronic units and data processing systems. The refractory rods, of different lengths, are partially coated with platinum at the lower ends designed for immersion into the melting. They are fixed to the shafts by a fast collars system which allows an easy substitution of the rods whenever necessary.

Other details of the invention will be apparent from the following description and claims and the accompanying drawing which, by way of illustration, shows a preferred embodiment of the present invention and the principles thereof and what is now considered to be the best mode contemplated for applying these principles.

BRIEF DESCRIPTION OF THE DRAWING

The drawing FIGURE is a sectional elevation view of the sensor head constructed in accordance with one embodiment of the invention.

DESCRIPTION OF THE PREFERRED EMBODIMENT

A metallic core (1) with cooling fins (2) fixed to a flanged base (17) is laid across by two vertical parallel shafts (3) concentric with two torque tubes (6) disposed therein. The lower ends of these shafts are slotted tubes (19) which secure two refractory rods (4) by fast collars (15). The rods are partially coated with platinum (14). The upper ends of the shafts are also slotted tubes (20) which fix by fast collars (16) the shafts of the rotors (5) belonging to two vibrating motors (21) fixed to a base (22). At the upper and at the lower ends of each shaft (3) are fixed discs (7) and (8), each of them connected mechanically to the fixed core through three fine rods (9), disposed at 120° angles around its central shaft. Upon the fixed plate (23) and the shafts (3) are installed the components of conventional sensors (10) having their outputs indicative of the angular position of shafts in relation to that fixed plate. These sensors (10) and motors (21) are closed inside an air-tight case (11) fixed to the core (1). At the top of this case there is a multi-contact plug (13) for electrical connection to the exterior units. Over the case (11) and fixed to the flanged base (17) is installed a metallic sleeve (12) open above, with a tube (18) beneath for the inlet of cooling air.

In operation the sensor head is installed on a rigid structure fixed over the channel where the molten glass flows, with both rods partially immersed into the melt in order that the refractory rods can be protected by the platinum coatings. Through the multi-contact plug, this sensor head is connected electrically to the control unit which contains conventional automatic control circuits, and also to a conventional data processing unit. The control unit powers the motors of the sensor head and controls the torsional vibration of the shafts maintaining each of them continuously vibrating at its own resonance frequency and at constant amplitude. To a certain value v of viscosity it is possible generate a voltage e1 by the control circuit associated to the first rod, in accordance with the equation:

$$e1 = eo1 + k1.v.L1 \qquad (1)$$

where $eo1=e1$ when $v=0$, L1 is the value of immersion of the rod and k1 is a constant dependent on its geometry in particular, on its diameter.

This voltage is therefore proportional to the viscosity and can be the basis for the generation of a proportional output for purposes of measurement, recording or control. Equation (1) shows however that in applications where the level of molten glass is subject to variations, the voltage e1 changes without changes in the viscosity v. An automatic compensation is therefore necessary. This compensation can be done through the voltage eo2 generated by the control circuit associated to the second rod and processed with the voltage eo1 in the processing unit in accordance with the equations system:

$$e1=eo1+k1.v.L1$$

$$e2=eo2+k2.v.L2$$

where eo2=e2 when v=0, L2 is the value of immersion of rod and k2 is a constant dependent on its geometry, in particular on its diameter. If by construction k1=k2=k and if L1−L2=L where L is the constant length difference of the rods, it is possible to get from the above equations:

$$v=((e1-e2)-(eo1-eo2))/kL \qquad (3)$$

$$L1=L(e1-eo1)/((e1-e2)-(eo1-eo2)) \qquad (4).$$

From these equations the processing unit and the control unit generate in real time the electrical signals proportional to the viscosity of the molten glass, independently of its level (equation 3), and to the immersion L1 which defines the level of the glass (equation 4). These signals can be used for purposes of measurement, recording or control.

Hence, while preferred embodiment of the invention has been described and illustrated, it is to be understood that other embodiments equivalents or obvious modifications based on the same or equivalent principles can be done by specialists without any result to jeopardize however the validity of the present invention and that any such other embodiments, modifications or equivalents are understood to fall within the scope of the following claims.

COMPONENT LIST

1—Metallic core
2—Fins
3—Shafts
4—Refractory rods
5—Rotors
6—Torque tubes
7—Metallic discs
8—Metallic discs
9—Fine rods
10—Conventional sensor of angular position
11—Air-tight case
12—Metallic sleeve
13—Multi-contact plug
14—Platinum coated end
15—Lower fast collar
16—Upper fast collar
17—Flanged base
18—Tube
19—Lower shaft slotted end
20—Upper shaft slotted end
21—Motors
22—Motors base
23—Fixed plate

What is claimed is:

1. A device for the on-line measurement of viscosity of molten glass comprising a sensor head formed by a fixed metallic core with external fins for air cooling, laid across by two vertical parallel shafts designed for torsional vibration, to which are fixed, at the lower slotted ends, two refractory rods partially coated with platinum and, at the upper slotted ends, the rotors of two motors fixed to a base designed for the torsional vibration of the vertical shafts, the crossing of the core by each of the shafts being done by a torque tube in such a way that a mechanical sealing is formed between its lower end at which is fixed one refractory rod by a fast collar and the upper end at which is fixed by other fast collar the rotor of each motor, each shaft being mechanically connected to two metallic discs, one at the upper end the other at the lower end, each of these discs being mechanically connected to the core by three fine rods disposed 120° around that central shaft.

2. A device for the on-line measurement of molten glass according to claim 1, comprising one conventional sensor of the angular position of each shaft in relation to a fixed plate, installed at the upper end of each shaft, the sensors and motors being closed inside an air-tight case with a multi-contact plug for the electrical connection to exterior units of control and data processing, this case being covered by a metallic sleeve open above and fixed to a flanged base with a tube beneath for the inlet of cooling air.

3. A device for the on-line measurement of molten glass in accordance with claim 1 or 2, comprising vibrant rods of different lengths in such a way that the voltages generated by the control circuits associated with those rods and processed by the exterior conventional processing unit originate the value of the viscosity independently of the variations of the glass level and/or the value of the glass level.

* * * * *